United States Patent
Qi et al.

(10) Patent No.: US 10,570,133 B2
(45) Date of Patent: Feb. 25, 2020

(54) SIMPLE PROCESS FOR PREPARING AN INTERMEDIATE FOR AVIBACTAM

(71) Applicant: XINFA PHARMACEUTICAL CO., LTD, Dongying (CN)

(72) Inventors: Yuxin Qi, Dongying (CN); Xinfa Li, Dongying (CN); Baolin Wang, Dongying (CN); Xin Xu, Dongying (CN); Yinlong Zhao, Dongying (CN); Yuqi Teng, Dongying (CN)

(73) Assignee: XINFA PHARMACEUTICAL CO., LTD, Dongying (CN)

( * ) Notice: Subject to any disclaimer, the term of this patent is extended or adjusted under 35 U.S.C. 154(b) by 0 days.

(21) Appl. No.: 16/345,752

(22) PCT Filed: Mar. 23, 2018

(86) PCT No.: PCT/CN2018/080309
§ 371 (c)(1),
(2) Date: Apr. 29, 2019

(87) PCT Pub. No.: WO2019/075990
PCT Pub. Date: Apr. 25, 2019

(65) Prior Publication Data
US 2019/0263813 A1 Aug. 29, 2019

(30) Foreign Application Priority Data
Oct. 18, 2017 (CN) .......................... 2017 1 0968330

(51) Int. Cl.
*C07D 471/08* (2006.01)
*C07D 211/60* (2006.01)
*A61K 31/437* (2006.01)
*A61P 31/04* (2006.01)
*C07B 57/00* (2006.01)

(52) U.S. Cl.
CPC .......... *C07D 471/08* (2013.01); *A61K 31/437* (2013.01); *A61P 31/04* (2018.01); *C07B 57/00* (2013.01); *C07D 211/60* (2013.01)

(58) Field of Classification Search
CPC ............................. C07D 471/08; C07D 211/60
USPC ......................................................... 546/121
See application file for complete search history.

(56) References Cited

U.S. PATENT DOCUMENTS

| | | | | |
|---|---|---|---|---|
| 7,112,592 B2 * | 9/2006 | Lampilas | ............. | C07D 487/08 514/300 |
| 7,612,087 B2 * | 11/2009 | Aszodi | ................. | A61K 31/439 514/300 |
| 8,916,709 B2 * | 12/2014 | Gu | ....................... | C07D 471/08 546/183 |
| 8,969,566 B2 * | 3/2015 | Ronsheim | ............ | C07D 211/60 546/121 |
| 2015/0315145 A1* | 11/2015 | Hirai | ....................... | C07B 53/00 546/84 |

FOREIGN PATENT DOCUMENTS

| | | | |
|---|---|---|---|
| CN | 106749242 | * | 5/2017 |
| CN | 106866668 | * | 6/2017 |

* cited by examiner

*Primary Examiner* — Niloofar Rahmani
(74) *Attorney, Agent, or Firm* — CBM Patent Consulting, LLC

(57) ABSTRACT

A compound of Formula III as the raw material is hydrolyzed in an alkaline condition, then acidized to prepare a compound of Formula IV, and the resulting compound of formula IV and a solid phosgene or diphosgene are concurrently subjected to the urea cyclization and the chloroformylation reaction in the presence of an organic base and a catalyst to obtain a compound of formula V, and then the compound of formula V is amidated to obtain the final product (II). In the present invention, a "one-pot" method is adopted for urea cyclization, chloroformylation, and amidation reaction, and the intermediate products do not need post-treatments such as separation and purification.

18 Claims, No Drawings

SIMPLE PROCESS FOR PREPARING AN INTERMEDIATE FOR AVIBACTAM

FIELD

The present invention relates to the field of pharmaceutical biochemical engineering, specifically relates to a simple process for preparing an intermediate for avibactam, and more particularly relates to a simple process for preparing (2S,5R)-6-benzyloxy-7-oxo-1,6-diazabicyclo[3.2.1]octane-2-carboxamide.

BACKGROUND

As a non-β-lactam inhibitor, one of diazabicyclooctanone compounds, avibactam may inhibit type A (including ESBL and KPC) and type C β-lactamases. When administered in combination with various types of cephalosporins and carbapenem antibiotics, avibactam has a broad spectrum activity against bacteria, particularly has a significant activity against the *Escherichia coli* and *Klebsiella pneumoniae* containing ultra-broad spectrum R-lactamases, *Escherichia coli* containing excessive AmpC enzyme, and *Escherichia coli* containing both AmpC and ultra-broad spectrum β-lactamases. Avibactam (I), with the CAS No. 1192491-61-4 and the chemical name of [(1R,2S,5R)-2-(aminocarbonyl)-7-oxo-1,6-diazabicyclo[3.2.1]oct-6-yl] sodium sulphate, has a structural formula represented in Formula I:

In patent literatures CN103649051A, CN105294690A, CN106866668A, WO2012086241, U.S. Pat. Nos. 8,148,540, 9,284,273, and 9,567,335, avibactam (I) was all prepared by using (2S,5R)-6-benzyloxy-7-oxo-1,6-diazabicyclo[3.2.1]octane-2-carboxamide (II) as an intermediate. The (2S,5R)-6-benzyloxy-7-oxo-1,6-diazabicyclo[3.2.1]octane-2-carboxamide (II) was debenzylated under palladium-on-carbon catalyzation in the presence of different reducing agents (such as hydrogen, triethylsilane, sodium formate, and hydrazine hydrate), then sulfated by the sulfur trioxide complex and salinized into quaternized ammonium, followed by ion exchange to obtain avibactam (I), as shown in Scheme 1.

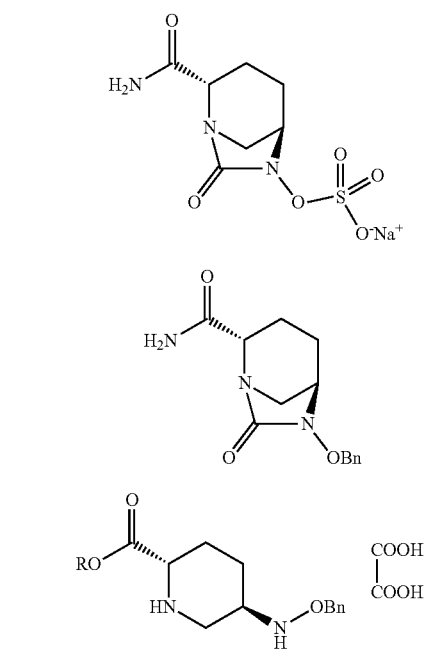

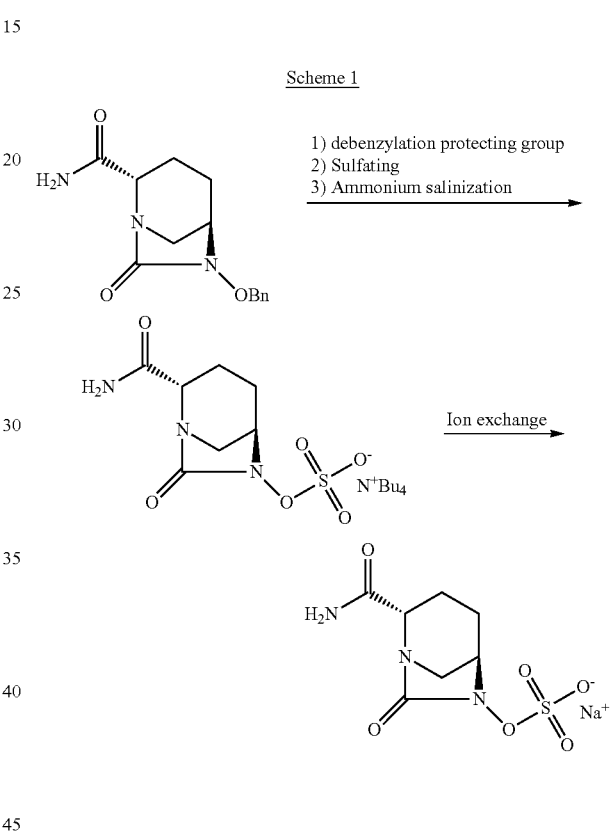

Various processes for preparing (2S,5R)-6-benzyloxy-7-oxo-1,6-diazabicyclo[3.2.1]octane-2-carboxamide (II) are mainly divided into two schemes: amidation followed by urea cyclization, and urea cyclization followed by amidation, as shown in Scheme 2:

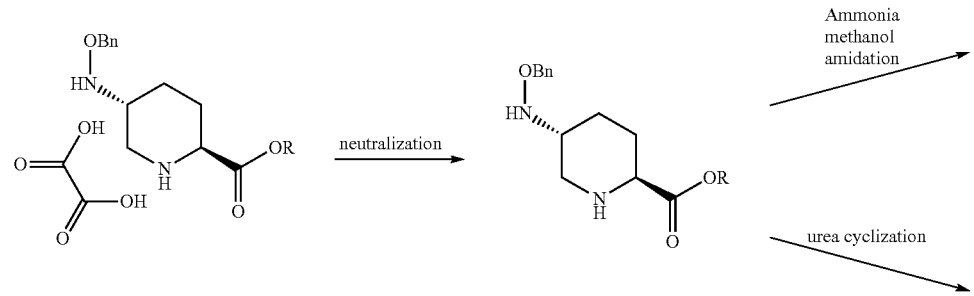

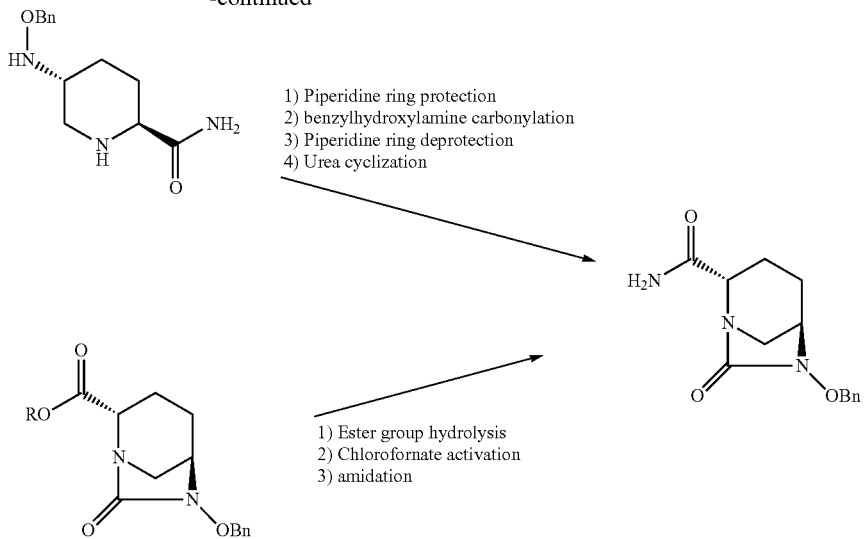

-continued

1) Piperidine ring protection
2) benzylhydroxylamine carbonylation
3) Piperidine ring deprotection
4) Urea cyclization 1) Ester group hydrolysis
2) Chlorofornate activation
3) amidation The patents CN103649051A and CN105294690A adopted the scheme of amidation followed by urea cyclization. 5R-[(benzyloxy)amino]piperidine-2S-carboxylate oxalate (III) as the raw material was amidated in a methanol solution of ammonia gas or an aqueous ammonia alcohol solution and the reaction mixture was filtered to remove annomium oxalate, the ammonium oxalate filter cake was washed with methanol and the resulting methanol solution was concentrated, the product was extracted with methylbenzene, and recrystallized with an appropriate solvent to obtain (2S,5R)-5-[(benzyloxy)amino]piperidine-2-carboxamide (yield: 68-99%); then, a carbonylation reaction between carbonyl diimidazole and benzyloxylamine was carried out under the protection of the amino on the piperidine ring of the resulting (2S,5R)-5-[(benzyloxy)amino]piperidine-2-carboxamide with 9-fluorenylmethyl chloroformate (FMOC-Cl), and after the removal of the protection group on the piperidine ring using diethylamine urea cyclization was carried out to obtain (2S,5R)-6-benzyloxy-7-oxo-1,6-diazabicyclo[3.2.1]octane-2-carboxamide (II) (yield: 90%, total yield: 61.2-89.1%). In that preparation process, the post-amidation treatment is complicated; and the protecting agent 9-fluorenylmethyl chloroformate used for urea cyclization is expensive. Besides, the 9-fluorenylmethyl chloroformate and the carbonyl diimidazole only provide one carbonyl, such that the reaction has a poor atom economy, which does not facilitate environment protection and cost reduction. Further, direct urea cyclization of (2S,5R)-5-[(benzyloxy) amino]piperidine-2-carboxamide using triphosgene and carbonyl diimidazole without protection of the amino on the piperidine ring has a low yield (50-56%) without industrial value.

Further, the patents CN102834395A, CN103649051A, CN103328476A, CN106279163A, CN106565712A, U.S. Pat. Nos. 9,284,273, and 9,567,335 all relate to a process of urea cyclization followed by amidation. 5R-[(benzyloxy) amino]piperidine-2S-carboxylate oxalate (III) as the raw material was urea cyclized using triphosgene-organic base, carbonyl diimidazole or other carbonylation agents, then hydrolyzed in an alkaline condition such as the aqueous lithium hydroxide to obtain (2S,5R)-6-benzyloxy-7-oxo-1, 6-diazabicyclo[3.2.1]octane-2-carboxylic acid; then, the carboxyl was activated into anhydride using trimethylacetyl chloride or other agents and then the anhydride was amidated using the aqueous ammonia to obtain (2S,5R)-6-benzyloxy-7-oxo-1,6-diazabicyclo[3.2.1]octane-2-carboxamide (II), with a total yield of 34.5-65.5%. The (2S,5R)-6-benzyloxy-7-oxo-1,6-diazabicyclo[3.2.1]octane-2-formate obtained by urea-cyclization has a low reactivity, which cannot be directly amidated in a methanol solution of ammonia gas. Instead, to be effectively amidated, the ester group needs to be hydrolyzed into the carboxyl, and then the carboxyl is activated into the anhydride. This process has a complicated operation procedure and a poor atom economy, which thus does not facilitate environment protection and industrial production.

SUMMARY

To address the drawbacks in the prior art, the present invention provides a simple process for preparing an intermediate for avibactam, namely (2S,5R)-6-benzyloxy-7-oxo-1,6-diazabicyclo[3.2.1]octane-2-carboxamide (II). The raw material for the present invention is inexpensive and easily accessible; the preparation process is simple and strongly operable without a need of a specific protecting agent or a carbonylation agent; besides, the reaction has a high atom economy and a low cost; the production process is green and environment-friendly; the resulting product (II) has a high purity and a high yield; the resulting (2S,5R)-6-benzyloxy-7-oxo-1,6-diazabicyclo[3.2.1]octane-2-carboxamide (II) may be used for preparing avibactam (I).

Definition of Terms

Compound of Formula III: 5R-[(benzyloxy) amino]piperidine-2S-carboxylate oxalate, wherein -Bn refers to benzyl;

Compound of Formula IV: 5R-[(benzyloxy) amino]piperidine-2S-carboxylic acid, wherein -Bn refers to benzyl;

Compound of Formula V: (2S,5R)-6-benzyloxy-7-oxo-1, 6-diazabicyclo[3.2.1]octane-2-formyl chloride, wherein -Bn refers to benzyl.

The numbering of the compounds in the specification is completely consistent with the numbering of their structural formulae, and they have same references.

A technical solution of the present invention is provided below:

A simple process for preparing an intermediate for avibactam, comprising the steps of:

(1) a compound of formula III is dissolved in solvent A, hydrolyzed in the presence of base A, and then acidized to obtain a compound of formula IV;

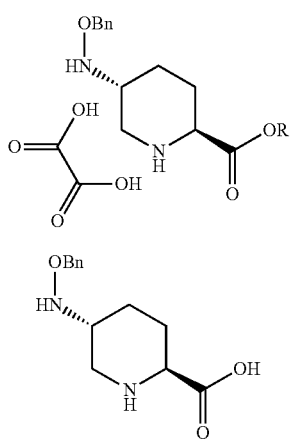

wherein R in the compound of formula III is $C_{1-6}$ aliphatic group or alkyl-substituted phenyl; preferably, R is one selected from the group consisting of methyl, ethyl, n-propyl, isopropyl, n-butyl, isobutyl, tert-butyl, n-pentyl, isopentyl, tert-pentyl, hexyl, benzyl, o-methylbenzyl and p-methylbenzyl;

2) the compound of formula IV and a solid phosgene or diphosgene are concurrently subjected to urea cyclization and chloroformylation reaction in the presence of organic base B and a catalyst in solvent B to obtain a compound of formula V which is directly used for the next step of reaction without purification;

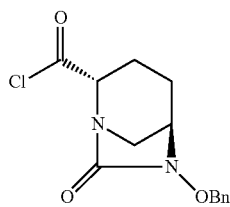

(3) an amidation reaction is carried out between the compound of formula V and ammonia to obtain (2S,5R)-6-benzyloxy-7-oxo-1,6-diazabicyclo[3.2.1]octane-2-carboxamide (II).

Preferably according to the present invention, after the compound of formula III in step (1) is hydrolyzed in an alkaline condition and acidized, an extract containing the compound of formula IV is obtained by an extracting agent; the extract containing the compound of formula IV is distilled to remove the extracting agent to obtain the compound of formula IV, or the extract containing the compound of formula IV is directly used for the next step of reaction without distillation.

Preferably according to the present invention, solvent A in step (1) is selected from the group consisting of dichloromethane, 1,2-dichloroethane, trichloromethane, tetrachloromethane, tetrahydrofuran, 2-methyltetrahydrofuran, methoxycyclopentane, methylbenzene and combinations of two or more thereof.

Preferably according to the present invention, in step (1), a mass ratio between solvent A and the compound of formula III is 3-4.5:1.

Preferably according to the present invention, in step (1), base A is selected from the group consisting of sodium hydroxide, potassium hydroxide, lithium hydroxide, potassium carbonate, sodium carbonate, potassium hydrogencarbonate, sodium hydrogencarbonate, and mixture of two or more thereof; preferably, base A is an aqueous solution containing the base at a concentration of 5-15% by mass.

Preferably according to the present invention, in step (1), a molar ratio between base A and the compound of formula III is 2.0-5.0:1.

Preferably according to the present invention, in step (1), the hydrolysis reaction is carried out at a temperature of 0-80° C.; preferably, in step (1), the hydrolysis reaction is carried out at a temperature of 10-40° C. The reaction tie is 2-5 hours.

Preferably, in step (1), the acidification is carried out at a temperature of 20-25° C. for 1-2 hours.

Preferably, in step (1), the acidification refers to adjusting the pH of the system to 2-3 by using an acidifying agent, the acidifying agent is an aqueous solution of hydrochloric acid, sulfuric acid or nitric acid at a concentration of 10-40% by mass.

Preferably, in step (2), solvent B is selected from the group consisting of dichloromethane, 1,2-dichloroethane, trichloromethane, tetrachloromethane, tetrahydrofuran, 2-methyltetrahydrofuran, methoxycyclopentane, methylbenzene, and combinations of two or more thereof.

Preferably according to the present invention, in step (2), a mass ratio between solvent B and the compound of formula IV is 4-20:1.

Preferably according to the present invention, in step (2), organic base B is selected from the group consisting of triethylamine, tri-n-butylamine, diisopropylethylamine, and combinations of two or more thereof.

Preferably according to the present invention, in step (2), the molar ratio between organic base B and the compound of formula IV is 3.0-8.0:1.

Preferably according to the present invention, in step (2), the catalyst is selected from the group consisting of N,N-dimetylformamide, pyridine, 4-dimethylaminopyridine, and combinations of two or more thereof.

Preferably according to the present invention, in step (2), the catalyst is present in 0.1-5.0% by mass of the compound of formula IV.

Preferably according to the present invention, in step (2), the molar ratio between the solid phosgene or diphosgene and the compound of formula IV is 0.6-2.5:1.

Preferably according to the present invention, the molar ratio between the solid phosgene and the compound of formula IV is 0.6-2.0:1.

Preferably according to the present invention, the molar ratio between the diphosgene and the compound of formula IV is 1.0-2.5:1.

Preferably according to the present invention, in step (2), the urea cyclization and the chloroformylation reaction are both carried out at a temperature of −20-60° C.; preferably, in step (2), the urea cyclization and the chloroformylation reaction are both carried out at a temperature of 0-40° C. The reaction tie is 1-8 hours.

Preferably according to the present invention, in step (3), the ammonia is selected from the group consisting of ammonia gas, a methanol solution of ammonia gas, or aqueous ammonia.

Preferably according to the present invention, in step (3), the molar ratio between the ammonia and the compound of formula IV is 1.0-5.0:1.

Preferably according to the present invention, in step (3), the amidation reaction is carried out at a temperature of −20-80° C.; preferably, in step (3), the amidation reaction is carried out at a temperature of 10-50° C. The reaction tie is 1-6 hours.

In the present invention, 5R-[(benzyloxy) amino]piperidine-2S-carboxylate oxalate (III) as the raw material is hydrolyzed in an alkaline condition, then acidized to obtain 5R-[(benzyloxy) amino]piperidine-2S-carboxylic acid (IV), and the resulting compound of formula IV and a solid phosgene or diphosgene are concurrently subjected to the urea cyclization and the chloroformylation reaction in the presence of the organic base and the catalyst to obtain (2S,5R)-6-benzyloxy-7-oxo-1,6-diazabicyclo[3.2.1]octane-2-formyl chloride (V), which is then amidated to obtain (2S,5R)-6-benzyloxy-7-oxo-1,6-diazabicyclo[3.2.1]octane-2-carboxamide (II), wherein the urea cyclization, the chloroformylation and the amidation reaction are carried out in a "one-pot" process, and the intermediate products do not need to be separated and purified. The Scheme (Scheme 3) is provided below:

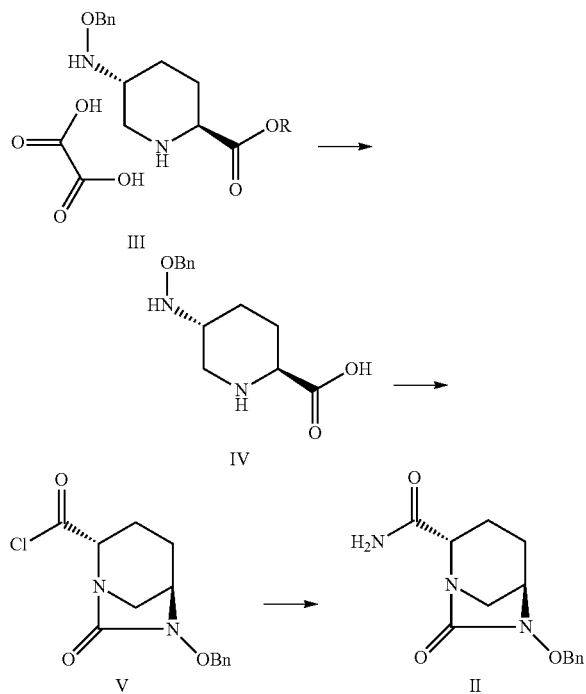

The present invention provides the following beneficial effects:

1. Compared with the prior arts, the present invention avoids the drawbacks of the process of amidation followed by urea cyclization, which requires protecting the piperidine ring and using a specific carbonylation agent, and further avoids the complicated operations of urea cyclization followed by amidation, which requires hydrolyzing ester group, activating into anhydride, and amidating. The present invention adopts a "one-pot" process for urea cyclization, chloroformylation, and amidation reaction, and the intermediate products do not need post-treatments such as separation and purification; the process has simple steps, green and environment-friendly procedures, and a low cost.

2. The present invention uses an inexpensive and easily accessible raw material and the types of reactions involved are typical ones; the reaction conditions are easily controllable; the operations are simple; the operability is strong; and the process is simple. The urea cyclization procedure needs no specific protection agent or carbonylation reagent; the reaction has a high atom economy; the production process is green and environment-friendly; and the product obtained from the urea cyclization has an appropriate reactivity, which may be amidated by ammonia gas, aqueous ammonia and the like, such that the steps are simple and the cost is low. Besides, the (2S,5R)-6-benzyloxy-7-oxo-1,6-diazabicyclo[3.2.1]octane-2-carboxamide (II) prepared according to the process of the present invention has a high purity and a high yield, which facilitates cost reduction and green production of avibactam (I).

EXAMPLES

Hereinafter, the present invention will be illustrated in detail with reference to the examples; however, the present invention is not limited thereto.

The percentages in the examples all refer to mass percentages, unless otherwise indicated.

The raw material 5R-[(benzyloxy) amino]piperidine-2S-carboxylate oxalate (Ill) is commercially available (Jinan Qinsi Pharmaceutical Company), which is a white powder with an optical purity of 99.6%.

The reaction process and product purity are monitored by a gas chromatograph or a liquid chromatograph. A liquid chromatograph equipped with a chiral column (ES-OVS, 150 mm×4.6 mm, Agilent) is used to detect the optical purity (area ratio %) and calculate the yield and e.e % value.

Example 1: Preparation of 5R-[(benzyloxy) amino]piperidine-2S-carboxylic acid (IV)

To a 500 ml 4-neck flask equipped with a stirrer and a thermometer, 150 g of dichloromethane, 150 g of 10% (mass) aqueous solution of sodium hydroxide and 43.0 g (0.1 mol) of benzyl 5R-[(benzyloxy) amino]piperidine-2S-carboxylate oxalate (III) were added, and then the reaction mixture was stirred at 20-30° C. for 3 hours. Then the reaction mixture was acidified to a pH value of 2.5-3.0 by 30% (mass) aqueous solution of hydrochloric acid, and stirred at a room temperature for 1-2 hours. The mixed solution was separated and then the aqueous phase was extracted thrice by dichloromethane (50 g each). The organic phases were combined and washed once by 20 g of saturated solution of sodium chloride. After the solvent was recovered from the obtained organic phase, 24.5 g of 5R-[(benzyloxy) amino]piperidine-2S-carboxylic acid was obtained in a yield of 98.0% and a purity of 99.9% in HPLC.

NMR (Nuclear Magnetic Resonance) data of the resulting product are provided below: $^1$H-NMR (400 MHz, DMSO-d6) δ: 1.10 (1H, q), 1.27 (1H, q), 1.82 (2H, d), 2.23 (1H, t), 2.76 (1H, m), 2.90 (1H, d), 3.13 (1H, d), 4.70 (2H, s), 6.54 (1H, d), 7.35 (5H, m), 13.51 (1H, br).

Example 2: Preparation of 5R-[(benzyloxy) amino]piperidine-2S-carboxylic acid (IV)

To a 500 ml 4-neck flask equipped with a stirrer and a thermometer, 150 g of 1,2-dichloroethane, 80 g of 10%

(mass) aqueous solution of lithium hydroxide and 43.0 g (0.1 mol) of benzyl 5R-[(benzyloxy) amino]piperidine-2S-carboxylate oxalate (III) were added, and then the reaction mixture was stirred at 20-25° C. for 4 hours. Then the reaction mixture was acidified to a pH value of 2.5-3.0 by 30% (mass) aqueous solution of hydrochloric acid, and stirred at a room temperature for 1-2 hours. The mixed solution was separated and then the aqueous phase was extracted thrice by 1,2-dichloroethane (50 g each). The organic phases were combined and washed once by 20 g of saturated solution of sodium chloride. After the solvent was recovered from the obtained organic phase, 24.6 g of 5R-[(benzyloxy) amino]piperidine-2S-carboxylic acid was obtained in a yield of 98.5% and a purity of 99.9% in HPLC.

Example 3: Preparation of 5R-[(benzyloxy) amino]piperidine-2S-carboxylic acid (IV)

To a 500 ml 4-neck flask equipped with a stirrer and a thermometer, 150 g of dichloromethane, 120 g of 10% (mass) aqueous solution of sodium hydroxide and 37.0 g (0.1 mol) of ethyl 5R-[(benzyloxy) amino]piperidine-2S-carboxylate oxalate (III) were added and then the reaction mixture was stirred at 20-25° C. for 4 hours. Then the reaction mixture was acidified to a pH value of 2.5-3.0 by 30% (mass) aqueous solution of hydrochloric acid, and stirred at a room temperature for 1-2 hours. The mixed solution was separated and then the aqueous phase was extracted thrice by dichloromethane (50 g each). The organic phases were combined and washed once by 20 g of saturated solution of sodium chloride. After the solvent was recovered from the obtained organic phase, 24.1 g of 5R-[(benzyloxy) amino]piperidine-2S-carboxylic acid was obtained in a yield of 96.4% and a purity of 99.9% in HPLC.

Example 4: Preparation of 5R-[(benzyloxy) amino]piperidine-2S-carboxylic acid (IV)

To a 500 ml 4-neck flask equipped with a stirrer and a thermometer, 150 g of dichloromethane, 150 g of 10% (mass) aqueous solution of sodium hydroxide and 39.5 g (0.1 mol) of tert-butyl 5R-[(benzyloxy) amino]piperidine-2S-carboxylate oxalate (III) were added, and then the reaction mixture was stirred at 20-30° C. for 3 hours. Then the reaction mixture was acidified to a pH value of 2.5-3.0 by 30% (mass) aqueous solution of hydrochloric acid, and stirred at a room temperature for 1-2 hours. The mixed solution was separated and then the aqueous phase was extracted thrice by dichloromethane (50 g each). The organic phases were combined and washed once by 20 g of saturated solution of sodium chloride. After the solvent was recovered from the obtained organic phase, 24.3 g of 5R-[(benzyloxy) amino]piperidine-2S-carboxylic acid was obtained in a yield of 97.2% and a purity of 99.9% in HPLC.

Example 5: Preparation of (2S,5R)-6-benzyloxy-7-oxo-1,6-diazabicyclo[3.2.1]octane-2-carboxamide (II)

To a 500 ml 4-neck flask equipped with a stirrer and a thermometer, 200 g of tetrahydrofuran, 12.5 g (0.05 mol) of 5R-[(benzyloxy) amino]piperidine-2S-carboxylic acid prepared in Example 2, 50 g of tri-n-butylamine, and 0.1 g of N,N-dimetylformamide were added. After cooling, a solution of 23.8 g (0.08 mol) of solid phosgene in 80 g of tetrahydrofuran was added dropwise at −10-0° C. After completion of the addition, the reaction mixture was stirred at 10-20° C. for 4 hours. 3.0-3.5 g of ammonia gas was introduced at 10-20° C. The reaction mixture was then stirred at 15-20° C. for 3 hours. The reaction liquid was poured into 300 g of ice-water mixture and separated; and then the aqueous phase was extracted twice by dichloromethane (50 g each). The organic phases were combined and washed twice by a saturated solution of sodium chloride (20 g each). After the solvent was recovered from the obtained organic phase, 10.0 g of cold chlorobutane was added; the mixture was then mashed, washed, and filtered to obtain 12.6 g of (2S,5R)-6-benzyloxy-7-oxo-1,6-diazabicyclo[3.2.1]octane-2-carboxamide in a yield of 91.6% and a purity of 99.9% in HPLC.

NMR (Nuclear Magnetic Resonance) data of the resulting product are provided below: $^1$H-NMR (400 MHz, DMSO-d6) δ: 1.65 (2H, m), 1.84 (1H, br), 2.06 (1H, m), 2.90 (2H, s), 3.62 (1H, s), 3.68 (1H, d), 4.93 (2H, dd), 7.30-7.46 (7H, m).

Example 6: Preparation of (2S,5R)-6-benzyloxy-7-oxo-1,6-diazabicyclo[3.2.1]octane-2-carboxamide (II)

To a 500 ml 4-neck flask equipped with a stirrer and a thermometer, 200 g of dichloromethane, 12.5 g (0.05 mol) of 5R-[(benzyloxy) amino]piperidine-2S-carboxylic acid prepared in Example 2, 60 g of diisopropylethylamine, and 0.1 g of N,N-dimetylformamide were added. After cooling, a solution of 23.8 g (0.08 mol) of solid phosgene in 80 g of dichloromethane was added dropwise at −10-0° C. After completion of the addition, the reaction mixture was stirred at 10-20° C. for 4 hours. 25 g of 10% (mass) methanol solution of ammonia gas was added at 10-20° C. The reaction mixture was then stirred at 15-20° C. for 3 hours. The reaction liquid was poured into 300 g of ice-water mixture and separated; and then the aqueous phase was extracted twice by dichloromethane (50 g each). The organic phases were combined and washed twice by a saturated solution of sodium chloride (20 g each). After the solvent was recovered from the obtained organic phase, 10.0 g of cold chlorobutane was added; the mixture was then mashed, washed, and filtered to obtain 12.7 g of (2S,5R)-6-benzyloxy-7-oxo-1,6-diazabicyclo[3.2.1]octane-2-carboxamide in a yield of 92.5% and a purity of 99.9% in HPLC.

Example 7: Preparation of (2S,5R)-6-benzyloxy-7-oxo-1,6-diazabicyclo[3.2.1]octane-2-carboxamide (II)

To a 500 ml 4-neck flask equipped with a stirrer and a thermometer, 200 g of dichloromethane, 12.5 g (0.05 mol) of 5R-[(benzyloxy) amino]piperidine-2S-carboxylic acid prepared in Example 2, 60 g of diisopropylethylamine, and 0.1 g of N,N-dimetylformamide were added. After cooling, a solution of 24.0 g (0.12 mol) of diphosgene in 60 g of dichloromethane was added dropwise at −10-0° C. After completion of the addition, the reaction mixture was stirred at 20-25° C. for 3 hours. 25 g of 10% (mass) methanol solution of ammonia gas was added at 20-25° C. The reaction mixture was then stirred at 20-25° C. for 3 hours. The reaction liquid was poured into 300 g of ice-water mixture and separated; and then the aqueous phase was extracted twice by dichloromethane (50 g each). The organic phases were combined and washed twice by a saturated solution of sodium chloride (20 g each). After the solvent was recovered from the obtained organic phase, 10.0 g of cold chlorobutane was added; the mixture was then mashed, washed, and filtered to obtain 12.5 g of (2S,5R)-6-benzyloxy-7-oxo-1,6-diazabicyclo[3.2.1]octane-2-carboxamide in a yield of 91.0% and a purity of 99.9% in HPLC.

Example 8: Preparation of (2S,5R)-6-benzyloxy-7-oxo-1,6-diazabicyclo[3.2.1]octane-2-carboxamide (II)

To a 500 ml 4-neck flask equipped with a stirrer and a thermometer, 200 g of dichloromethane, 12.5 g (0.05 mol) of 5R-[(benzyloxy) amino]piperidine-2S-carboxylic acid prepared in Example 2, 40 g of triethylamine, and 0.1 g of N,N-dimetylformamide were added. After cooling, a solution of 23.8 g (0.08 mol) of solid phosgene in 80 g of dichloromethane was added dropwise at −10-0° C. After completion of the addition, the reaction mixture was stirred for 4 hours at a temperature of 10-20° C. 25 g of 10% (mass) aqueous ammonia was added at 10-20° C. The reaction mixture was then stirred at 15-20° C. for 3 hours. The reaction liquid was poured into 200 g of ice-water mixture and separated; and then the aqueous phase was extracted twice by dichloromethane (50 g each). The organic phases were combined and washed twice by a saturated solution of sodium chloride (20 g each). After the solvent was recovered from the obtained organic phase, 10.0 g of cold chlorobutane was added; the mixture was then mashed, washed, and filtered to obtain 12.1 g of (2S,5R)-6-benzyloxy-7-oxo-1,6-diazabicyclo[3.2.1]octane-2-carboxamide in a yield of 88.0% and a purity of 99.8% in HPLC.

Example 9: Preparation of (2S,5R)-6-benzyloxy-7-oxo-1,6-diazabicyclo[3.2.1]octane-2-carboxamide (II)

In preparation of 5R-[(benzyloxy) amino]piperidine-2S-carboxylic acid (IV), the mixed liquid of resulting organic phase is directly subjected to the following steps of:

To a 500 ml 4-neck flask equipped with a stirrer and a thermometer, 150 g of dichloromethane, 120 g of 10% (mass) aqueous solution of sodium hydroxide and 37.0 g (0.1 mol) of ethyl 5R-[(benzyloxy) amino]piperidine-2S-carboxylate oxalate (Ill) were added, and then the reaction mixture was stirred at 20-25° C. for 4 hours. Then the reaction mixture was then acidified to a pH value of 2.5-3.0 by 30% (mass) aqueous solution of hydrochloric acid, and stirred at a room temperature for 1-2 hours. The mixed solution was separated and then the aqueous phase was extracted thrice by dichloromethane (50 g each). The organic phases were combined to obtain an organic phase mixed solution.

The obtained organic phase mixed solution was transferred to another 500 ml 4-neck flask to which 60 g of diisopropylethylamine and 0.1 g of N,N-dimethylformamide were charged. After cooling, a solution of 26.7 g (0.09 mol) of solid phosgene in 80 g of dichloromethane was added dropwise at −10-0° C. After completion of the addition, the reaction mixture was stirred at 10-20° C. for 4 hours. 25 g of 10% (mass) methanol solution of ammonia gas was added at 10-20° C. The reaction mixture was then stirred at 15-20° C. for 3 hours. The reaction liquid was poured into 300 g of ice-water mixture and separated; and then the aqueous phase was extracted twice by dichloromethane (50 g each). The organic phases were combined and washed twice by a saturated solution of sodium chloride (20 g each). After the solvent was recovered from the obtained organic phase, 10.0 g of cold chlorobutane was added; the mixture was then mashed, washed, and filtered to obtain 24.9 g of (2S,5R)-6-benzyloxy-7-oxo-1,6-diazabicyclo[3.2.1]octane-2-carboxamide in a total yield of 90.5% and a purity of 99.9% in HPLC.

Comparative Example 1: Preparation of 5R-[(benzyloxy) amino]piperidine-2S-carboxylic acid (IV)

To a 500 ml 4-neck flask equipped with a stirrer and a thermometer, 150 g of dichloromethane, 70 g of 10% (mass) aqueous solution of sodium hydroxide and 43.0 g (0.1 mol) of benzyl 5R-[(benzyloxy) amino]piperidine-2S-carboxylate oxalate (III) were added, and then the reaction mixture was stirred at 20-30° C. for 3 hours. The reaction mixture was then acidified to a pH value of 2.5-3.0 by 30% (mass) aqueous solution of hydrochloric acid, and stirred at a room temperature for 1-2 hours. The mixed solution was separated and then the aqueous phase was extracted thrice by dichloromethane (50 g each). The organic phases were combined and washed once by 20 g of saturated solution of sodium chloride. After the solvent was recovered from the obtained organic phase, 9.5 g of 5R-[(benzyloxy) amino]piperidine-2S-carboxylic acid was obtained in a yield of 38.1% and a purity of 98.1% in HPLC.

This comparative example shows that during the procedure of preparing 5R-[(benzyloxy) amino]piperidine-2S-carboxylic acid, if the amount of base is too low, the hydrolysis will be incomplete, causing significant decrease of the yield of 5R-[(benzyloxy) amino]piperidine-2S-carboxylic acid.

Comparative Example 2: Preparation of 5R-[(benzyloxy) amino]piperidine-2S-carboxylic acid (IV)

To a 500 ml 4-neck flask equipped with a stirrer and a thermometer, 150 g of dichloromethane, 150 g of 10% (mass) aqueous solution of sodium hydroxide and 43.0 g (0.1 mol) of benzyl 5R-[(benzyloxy) amino]piperidine-2S-carboxylate oxalate (III) were added, and then the reaction mixture was stirred at 20-30° C. for 3 hours. The reaction mixture was then acidified to a pH value of 1.5-1.9 by 30% (mass) aqueous solution of hydrochloric acid, and stirred at a room temperature for 1-2 hours. The mixed solution was separated and then the aqueous phase was extracted thrice by dichloromethane (50 g each). The organic phases were combined and washed once by 20 g of saturated solution of sodium chloride. After the solvent was recovered from the obtained organic phase, 18.2 g of 5R-[(benzyloxy) amino] piperidine-2S-carboxylic acid was obtained in a yield of 72.8% and a purity of 99.7% in HPLC.

This comparative example shows that during the procedure of preparing 5R-[(benzyloxy) amino]piperidine-2S-carboxylic acid, if the pH value for the acidification is too low, a part of the product will be converted into hydrochloride that is dissolved in water, causing a decrease of the yield of 5R-[(benzyloxy) amino]piperidine-2S-carboxylic acid.

What is claimed is:
1. A simple process for preparing an intermediate for avibactam, comprising the steps of:
 (1) a compound of formula III is dissolved in solvent A, hydrolyzed in the presence of base A, and then acidized to obtain a compound of formula IV;

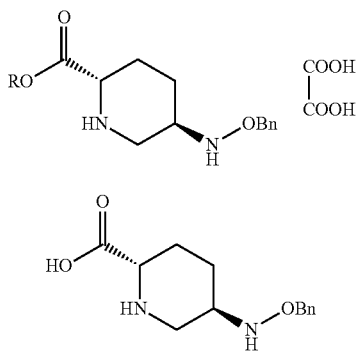

wherein R in the compound of formula III is $C_{1-6}$ aliphatic group or phenyl substituted with alkyl; preferably, R is selected from the group consisting of methyl, ethyl, n-propyl, isopropyl, n-butyl, isobutyl, tert-butyl, n-pentyl, isopentyl, tert-pentyl, hexyl, benzyl, o-methylbenzyl and p-methylbenzyl;

2) the compound of formula IV and a solid phosgene or diphosgene are concurrently subjected to urea cyclization and chloroformylation reaction in the presence of organic base B and a catalyst in solvent B to obtain a compound of formula V which is directly used for the next step of reaction without purification;

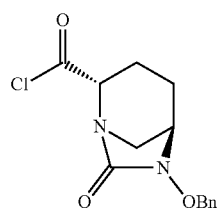

(3) an amidation reaction is carried out between the compound of formula V and ammonia to obtain (2S, 5R)-6-benzyloxy-7-oxo-1,6-diazabicyclo[3.2.1]octane-2-carboxamide (II) with a purity of 99.8-99.9%.

2. The simple process for preparing the intermediate for avibactam according to claim 1, wherein after the formula III in step (1) is hydrolyzed in an alkaline condition and acidized, an extract containing the compound of formula IV is obtained by an extracting agent; the extract containing the compound of formula IV is distilled to remove the extracting agent to obtain the compound of formula IV, or the extract containing the compound of formula IV is directly used for the next step of reaction without distillation.

3. The simple process for preparing the intermediate for avibactam according to claim 1, wherein solvent A in step (1) is selected from the group consisting of dichloromethane, 1,2-dichloroethane, trichloromethane, tetrachloromethane, tetrahydrofuran, 2-methyltetrahydrofuran, methoxycyclopentane, methylbenzene and a combination of two or more thereof; in step (1), a mass ratio between solvent A and the compound of formula III is 3-4.5:1.

4. The simple process for preparing the intermediate for avibactam according to claim 1, wherein in step (1), the hydrolysis reaction is carried out at a temperature of 0-80° C.

5. The simple process for preparing the intermediate for avibactam according to claim 1, wherein in step (1), the acidification refers to adjusting the pH of the system to 2-3 by an acidifying agent.

6. The simple process for preparing the intermediate for avibactam according to claim 1, wherein in step (2), solvent B is selected from the group consisting of dichloromethane, 1,2-dichloroethane, trichloromethane, tetrachloromethane, tetrahydrofuran, 2-methyltetrahydrofuran, methoxycyclopentane, methylbenzene and a combination of two or more thereof; in step (2), a mass ratio between solvent B and the compound of formula IV is 4-20:1.

7. The simple process for preparing the intermediate for avibactam according to claim 1, wherein in step (2), the molar ratio between the solid phosgene or diphosgene and the compound of formula IV is 0.6-2.5:1.

8. The simple process for preparing the intermediate for avibactam according to claim 1, wherein in step (2), the urea cyclization and the chloroformylation reaction are both carried out at a temperature of –20-60° C.

9. The simple process for preparing the intermediate for avibactam according to claim 1, wherein in step (3), the ammonia is selected from the group consisting of ammonia gas, a methanol solution of ammonia gas, or aqueous ammonia.

10. The simple process for preparing the intermediate for avibactam according to claim 1, wherein in step (3), the amidation reaction is carried out at a temperature of –20-80° C.

11. The simple process for preparing the intermediate for avibactam according to claim 3, wherein the base A is selected from the group consisting of sodium hydroxide, potassium hydroxide, lithium hydroxide, potassium carbonate, sodium carbonate, potassium hydrogencarbonate or sodium hydrogencarbonate, or a mixture of two or more thereof; and a molar ratio between base A and the compound of formula III is 2.0-5.0:1.

12. The simple process for preparing the intermediate for avibactam according to claim 4, wherein the acidification is carried out at a temperature of 20-25° C.

13. The simple process for preparing the intermediate for avibactam according to claim 5, wherein the acidifying agent is an aqueous solution of hydrochloric acid, sulfuric acid or nitric acid at a concentration of 10-40% by mass.

14. The simple process for preparing the intermediate for avibactam according to claim 6, wherein the organic base B is selected from the group consisting of triethylamine, tri-n-butylamine, diisopropylethylamine and a combination of two or more thereof; the molar ratio between the organic base B and the compound of formula IV is 3.0-8.0:1;
  the catalyst is selected from the group consisting of N,N-dimetylformamide, pyridine, 4-dimethylaminopyridine and a combination of two or more thereof; the catalyst is present in 0.1-5.0% by mass of the compound of formula IV.

15. The simple process for preparing the intermediate for avibactam according to claim 7, wherein the molar ratio between the solid phosgene and the compound of formula IV is 0.6-2.0:1;
  the molar ratio between the diphosgene and the compound of formula IV is 1.0-2.5:1.

16. The simple process for preparing the intermediate for avibactam according to claim 8, wherein the urea cyclization and the chloroformylation reaction are both carried out at a temperature of 0-40° C.

17. The simple process for preparing the intermediate for avibactam according to claim 9, wherein the molar ratio between the ammonia and the compound of formula IV is 1.0-5.0:1.

18. The simple process for preparing the intermediate for avibactam according to claim 10, wherein the amidation reaction is carried out at a temperature of 10-50° C.

* * * * *